United States Patent [19]

Weidmann

[11] Patent Number: 5,045,537

[45] Date of Patent: Sep. 3, 1991

[54] HYDROPHILIC RENIN INHIBITORS, THEIR PREPARATION AND USE

[75] Inventor: Beat Weidmann, Allschwil, Switzerland

[73] Assignee: Sandoz Ltd., Basel, Switzerland

[21] Appl. No.: 244,220

[22] Filed: Sep. 14, 1988

[30] Foreign Application Priority Data

Sep. 15, 1987 [DE] Fed. Rep. of Germany ....... 3730895

[51] Int. Cl.$^5$ ................. A61K 31/695; A61K 31/455; C07D 213/66; C07F 7/10
[52] U.S. Cl. ...................................... 514/63; 514/332; 514/356; 546/14; 546/255; 546/318; 546/322
[58] Field of Search ................. 546/14, 255, 318, 322; 514/278, 63, 332, 356

[56] References Cited

PUBLICATIONS

Cumin et al., "Biochem., Biophys. Acta", vol. 913, pp. 10–19, (1987).

*Primary Examiner*—Robert T. Bond
*Attorney, Agent, or Firm*—Gerald D. Sharkin; Robert S. Honor; Thomas O. McGovern

[57] ABSTRACT

Hydrophilic renin inhibitors, especially of formula

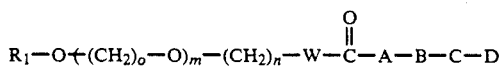

wherein $R_1$, W, o, m, n, A, B, C and D possess the definitions given in claim 2, processes for their production and their use in the treatment of hypertension, cardiac insufficiency and the treatment of diseases caused by retroviruses.

7 Claims, No Drawings

HYDROPHILIC RENIN INHIBITORS, THEIR PREPARATION AND USE

The present invention relates to novel hydrophilic renin inhibitors, their preparation and use as well as pharmaceutical compositions containing them.

Especially the invention provides hydrophilic renin inhibitors of formula

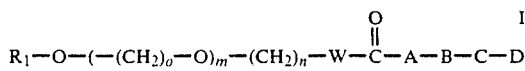

I wherein
- W is —O—, —NR$_2$— or —CH$_2$, whereby R$_2$ signifies hydrogen or a straight-chain or branched (C$_{1-5}$)alkyl radical,
- R$_1$ is hydrogen, a straight-chain or branched (C$_{1-20}$)alkyl radical or a sugar radical which is bonded as a glycoside; an optionally substituted, saturated or unsaturated, straight-chain or branched (C$_{2-30}$)alkylcarbonyl group, (C$_{3-6}$)polyhydroxyalkylcarbonyl-, a phosphoroyl-, a bis-(dimethylamino)-phosphoroyl-, a sulpho-, an aroyl-, a heteroaroyl-, an arylalkyl-, an arylalkylcarbonyl-, a heteroarylalkylcarbonyl- or a biotinyl group, or
- R$_1$ signifies a group of formula

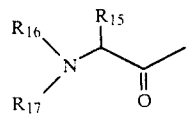

wherein
- R$_{15}$ is hydrogen or a side chain of a D- or L-amino acid, and
- R$_{16}$ and R$_{17}$ are the same or different and respectively signify hydrogen, (C$_{1-5}$)alkyl, (C$_{2-5}$)hydroxyalkyl or (C$_{2-5}$)aminoalkyl, or
- R$_1$ signifies a group of formula

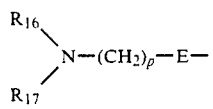

wherein
- R$_{16}$ and R$_{17}$ are defined as above,
- p denotes a whole number from 0 to 5 and
- E signifies a bond or the group

or
- R$_1$ signifies a group of formula

F—(CH$_2$)$_p$—E— wherein
- p and E are defined as above, and
- F denotes groups of formulae

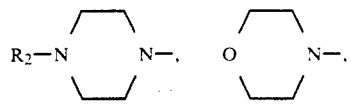

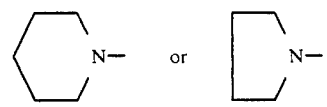

whereby
- R$_2$ is defined as above,
- m is a whole number from 1 to 20,
- n is a whole number from 0 to 5, and
- o is 2 or 3,
- A, B and C are the same or different and signify a bond or a group of formula

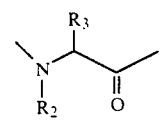

wherein
- R$_2$ is defined as above, and
- R$_3$ signifies a hydrophilic or lipophilic amino acid side chain, or
- R$_2$ and R$_3$ together form a —(CH$_2$)$_o$— chain, wherein o is defined as above,
- D signifies either a group of formula

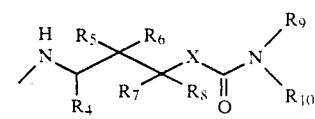

wherein
- R$_4$ has the same significance as R$_3$,
- R$_5$ is a hydroxyl or an amino group, and
- R$_6$ is hydrogen, or
- R$_5$ and R$_6$ together form an oxo group,
- R$_7$ and R$_8$, independently of one another, signify fluorine or hydrogen,
- R$_9$ and R$_{10}$ are the same or different and respectively signify hydrogen, a straight-chain or branched (C$_{1-5}$)-alkyl radical, or they respectively signify a group of formula

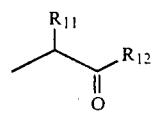

wherein
- R$_{11}$ signifies a straight-chain or branched (C$_{1-5}$)-alkyl radical or a straight-chain or branched (C$_{1-5}$)-hydroxyalkyl radical,
- R$_{12}$ is a hydroxyl radical, a straight-chain or branched (C$_{1-5}$)-alkoxy group, an amino group or a (C$_{1-5}$)-alkylamino group, an aminomethylpyridyl group, a benzyl group or a group of formula

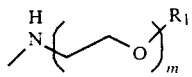

wherein $R_1$ and m are defined as above, or $R_1$ denote a protected or unprotected amino acid, X signifies a bond, or denotes

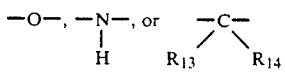

wherein $R_{13}$ and $R_{14}$, independently of one another, denote hydrogen or fluorine, or respectively possess the definition given above for $R_3$, or D signifies a group of formula

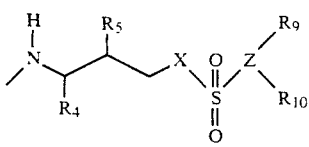

wherein $R_4$, $R_5$, $R_9$, $R_{10}$ and X possess the definitions given above, and Z is

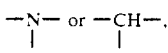

or

D signifies a group of formula

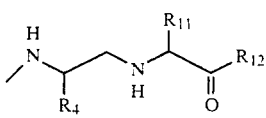

wherein $R_4$, $R_{11}$ and $R_{12}$ possess the definitions given above, and their salts.

Asymmetrically substituted carbon atoms may have R- or S-configuration. The configurations given in the following formula I$^y$ are preferred. The hydrophilic renin inhibitors are referred to hereinafter as compounds according to the invention.

In contrast to the conventional renin inhibitors, the compounds according to the invention are notable for advantageous hydrophilic properties, and are even partly water-soluble. The compounds according to the invention have high affinity for human renin even in the presence of plasma protein (i.e. they are only weakly bonded to plasma protein such as albumin etc.). These properties allow the compounds according to the invention to be advantageously differentiated from previously known renin inhibitors.

In $R_1$ of formula I a straight-chain or branched alkyl is especially an alkyl with 1 to 5 carbon atoms, especially ethyl, propyl or isobutyl, the sugar radical which is bonded as a glycoside is for example glucopyranosyl which may be optionally O-acylated, e.g. tetra-O-acetyl-glucopyranosyl, an optionally substituted saturated or unsaturated $(C_{2-30})$alkylcarbonyl group is in particular a corresponding $(C_{4-20})$alkylcarbonyl group, for example a palmitoyl, oleyl, linoyl, stearoyl or pivaloyl radical, whereby the alkylcarbonyl group may be substituted by a cyclopentaphenanthrene radical and may denote a cholyl radical, a $(C_{3-6})$polyhydroxyalkylcarbonyl radical is for example a glycerinoyl or a gluconoyl radical which may be optionally substituted, and may be for example a penta-O-acetylgluconoyl or dibutyroylglycerinoyl radical, an aroyl radical is for example the benzoyl radical, a heteroaroyl is for example the 2-, 3- or 4-pyridoyl radical, especially a 3-pyridoyl radical, an arylalkyl radical is for example the benzyl, phenethyl, naphthylmethyl, p-chlorophenoxypropyl-2 radical, an arylalkylcarbonyl radical is for example a phenylacetyl, bis(1-naphthylmethyl)acetyl or p-chlorophenoxy-1,1-dimethylacetyl radical, a heteroarylalkylcarbonyl group is for example a bis-(3-pyridylmethyl)acetyl or a bis(4-quinolinylmethyl)acetyl radical. In $R_{15}$, a side chain of a D- or L-amino acid is in particular methyl, isopropyl, isobutyl, benzyl, hydroxy($C_{1-5}$)alkyl, 4-aminobutyl or 2-carboxyethyl.

The hydrophilic or lipophilic amino acid side chain in the definition of $R_3$ may be for example a isopropyl, n-butyl, isobutyl, 2-butenyl, benzyl optionally substituted in paraposition by a methoxy group, a 4-imidazolylmethyl, 2-methylthioethyl, methylthiomethyl, trimethylsilylmethyl, cyclohexylmethyl, a 2-thienylmethyl-, an 1-adamantylmethyl or a pyridylmethyl radical or a halogen like e.g. chlorine.

Hydroxyalkyl with 1 to 5 carbon atoms is preferably hydroxyethyl or hydroxypropyl, and an alkoxy group with 1 to 5 carbon atoms preferably signifies methoxy or ethoxy.

Preferred compounds of formula I possess formula I$^y$

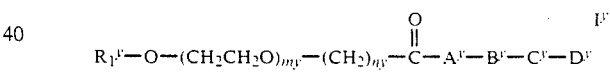

wherein $R_1{}^y$ signifies hydrogen, methyl or glucopyranosyl, $m^y$ signifies a whole number from 2 to 7 and $n^y$ signifies 0 or 1, $A^y$ signifies a bond or proline, $B^y$ signifies a group of formula.

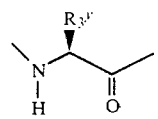

whereby $R_3{}^y$ signifies cyclohexylmethyl, benzyl, trimethylsilylmethyl, p-methoxybenzyl, 1-adamantylmethyl or isobutyl.

$C^y$ signifies a group of formula

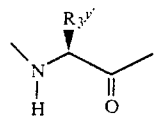

whereby $R_3y'$ is n-butyl, isobutyl, 2-butenyl, benzyl, 4-imidazolylmethyl or pyridylmethyl.

$D^y$ is a group of formula

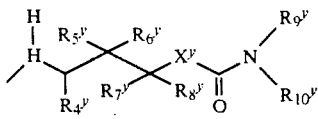

wherein $R_4^y$ is isobutyl, benzyl or cyclohexylmethyl, and either $R_5^y$ signifies a hydroxyl radical and $R_6^y$ signifies hydrogen where $R_7^y$ and $R_8^y$ respectively denote hydrogen, or $R_5^y$ and $R_6^y$ together form the oxo group where $R_7^y$ and $R_8^y$ respectively denote fluorine, $X^y$ signifies a bond or a group of formula

wherein either $R_{13}^y$ and $R_{14}^y$ respectively signify fluorine, or $R_{14}^y$ has the definition n-butyl, isobutyl, 2-butenyl, methylthiomethyl, benzyl, isopropyl or chlorine and $R_{13}^y$ denotes hydrogen, $R_9^y$ signifies hydrogen and $R_{10}^y$ signifies hydrogen, methyl, i-propyl, i-butyl, 2-butyl or a group of formula

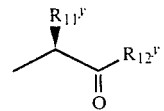

wherein $R_{11}^y$ denotes i-butyl or 2-butyl and $R_{12}^y$ denotes aminomethylpyridyl.

The preparation of compounds of formula I is characterised in that a) a compound of formula II,

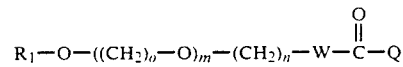

wherein $R_1$, W, o, m and n possess the definitions given above and Q denotes a hydroxyl or a p-nitrophenyl radical, is reacted with a compound of formula,

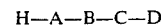

wherein A, B, C and D possess the definitions given above, or b) a compound of formula I, wherein $R_5$ is a hydroxyl radical and $R_6$ is hydrogen, is oxidised to a compound of formula I, wherein $R_5$ and $R_6$ together form an oxo group.

The process according to stage a) is preferably effected such that an acid of formula II (Q=OH) is reacted with an amine of formula III using processes which are known in peptide chemistry, e.g. in the presence of N,N'-dicyclohexylcarbodiimide or N-ethyl-N'-(3-dimethylaminopropyl)-carbodiimide (whilst adding 1-hydroxybenzotriazole) in a suitable solvent such as methylene chloride, at temperatures between 0° and room temperature. Alternatively, activated acid derivatives (Q=p-nitrophenyl) can also be reacted directly with the amine at temperatures between 20° and 80°.

The process according to stage b) is effected such that alcohols of the compounds of formula I are oxidised with a chromium trioxide dipyridine complex (Collin's reagent) in a solvent such as methylene chloride or dimethylformamide, to form the corresponding ketone.

The starting compounds used in the above processes are either known or may be produced by known processes, for example as described in the following examples.

The compounds of formula I produced according to the invention may be isolated and purified by known processes. Racemic and/or diastereoisomeric mixtures can be separated in known manner.

If the compounds of formula I contain acidic or basic groups, they may optionally also form salts, for example metal salts such as sodium salts or acid addition salts such as hydrochlorides.

In the following examples, all temperatures are given in degrees celsius and are uncorrected.

The compounds given in abbreviated form in the examples are written out fully in claim 4 in order of the examples beginning with Example 2.

In the following examples, the following abbreviations are used:

| | |
|---|---|
| H-Bly-OH | (2S)-2-amino-hex-(4)-ene-carboxylic acid |
| 3EG-OH | 3,6,9,12-tetraoxatridecanoic acid |
| 7EG-OH | 3,6,9,12,15,18,21,24-octaoxa-pentacosanic acid |
| PEG-OH | oligomeric mixture of polyoxacarboxylic acids |
| H-SO$_2$Chatin-OH | (2R,3S)-3-amino-4-cyclohexyl-2-hydroxy-butane-sulphonic acid |
| H-Cha(OH)Bly-OH | (2R,4S,5S)-5-amino-2-(E-2-butenyl)-6-cyclo-hexyl-4-hydroxy-caproic acid |
| H-Chatin-OH | (3S,4S)-4-amino-5-cyclohexyl-3-hydroxy-valeric acid |
| H-F$_2$Chatin-OH | (3R,4S)-4-amino-5-cyclohexyl-2,2-difluoro-3-hydroxy-valeric acid |
| H-F$_2$Chaton-OH | (4S)-4-amino-5-cyclohexyl-2,2-difluoro-3-oxo-valeric acid |
| H-Tmsal-OH | (2R)-2-amino-3-trimethylsilyl-propionic acid |
| H-4eg-OH | 2,5,8,11,14-pentaoxamyristic acid |
| Glyc-OH | β-D-glucopyranoside |
| AcGlyc-OH | 2,3,4,6-tetraacetyl-β-D-glucopyranoside |
| Stear-OH | stearic acid |
| Linol-OH | linoleic acid |
| Chol-OH | cholic acid |
| Dinac-OH | (bis-1-naphthylmethyl)-acetic acid |
| H-Cha-OH | (2S)-2-amino-3-cyclohexyl-propionic acid |
| H-Ada-OH | (2S)-2-amino-3-(1-adamantyl)-propionic acid |
| H-Thala-OH | (2S)-2-amino-3-(2-thienyl)propionic acid |
| Niacin | nicotinoyl |
| Tmpac | 3,4,5-trimethoxyphenylacetyl |
| Clof | (p-chlorphenoxy)dimethylacetyl |
| H-2eg-OH | 2,5,8-trioxaoctanic acid |
| H-3eg-OH | 2,5,8,11-tetraoxaundecanic acid |
| H-Cha(OH)Bualy-OH | (2R,4S,5S)-5-amino-2-N-butyl-amino-6-cyclo-hexyl-4-hydroxy-capronic acid |
| α-Pic | 2-aminomethyl-pyridine |

EXAMPLE 1

Peg-Phe-His-SO₂Chatin-NH₂

35 mg of H-Phe-His-SO₂Chatin-NH₂ are reacted in 0.5 ml of tetrahydrofuran with 10 mg of hydroxybenzotriazole, 60 mg of PEG-OH and 13 mg of N,N'-dicyclohexylcarbodiimide. After 15 hours, the precipitated dicyclohexylurea is filtered off, and the crude product is chromatographed on silica gel with methanol/methylene chloride (5:95).

EXAMPLE 2

7EG-Phe-His-Cha(OH)Bly-NHBu 55 mg of H-Phe-His-Cha(OH)Bly-NHBu are reacted analogously to example 1 with 20 mg of hydroxybenzotriazole, 33 mg of 7EG-OH and 18 mg of N,N'-dicyclohexylcarbodiimide in 0.5 ml of dimethylformamide. The crude product is precipitated from methanol/methylene chloride/ether. $[\alpha]_D^{20} = -20.9°$ (c=0.2 in $CH_2Cl_2$).

EXAMPLE 3

7EG-Phe-Nle-Chatin-Leu-α-picoline 100 mg of H-Phe-Nle-Cha-Leu-α-picoline are reacted analogously to example 1 with 20 mg of hydroxybenzotriazole, 59 mg of 7EG-OH and 31 mg of N,N'-dicyclohexylcarbodiimide. The product is crystallised from methylene chloride/ether/hexane. $[\alpha]_D^{20} = -4.8°$ (c=0.1 in $CH_2Cl_2$).

EXAMPLE 4

3EG-Phe-Nle-Chatin-Leu-α-picoline 100 mg of H-(Phe)-Nle-Chatin-Leu-α-picoline are reacted exactly as in example 1 with 20 mg of hydroxybenzotriazole, 33 mg of 3EG-OH and 31 mg of N,N'-dicyclohexylcarbodiimide. $[\alpha]_D^{20} = -5.2°$ (c=0.1 in $CH_2Cl_2$).

EXAMPLE 5

7EG-Pro-Phe-Nle-Chatin-Leu-α-picoline 78 mg of H-Pro-Phe-Nle-Chatin-Leu-α-picoline are reacted analogously to example 1 with 20 mg of hydroxybenzotriazole, 40 mg of 7EG-OH and 20 mg of N,N'-dicyclohexylcarbodiimide. The crude product is chromatographed on silica gel with methanol/methylene chloride (5:95). $[\alpha]_D^{20} = -30.3°$ (c=0.6 in $CH_2Cl_2$).

EXAMPLE 6

7EG-Tmsal-Bly-F₂Chatin-NHiBu 59 mg of H-Tmsal-Bly-F₂Chatin-NHiBu are reacted analogously to example 1 in 1 ml of methylene chloride/tetrahydrofuran (9:1) with 29 mg of hydroxybenzotriazole, 43 mg of 7EG-OH and 23 mg of N,N'-dicyclohexylcarbodiimide. The product is then chromatographed with methanol/methylene chloride (1 to 10%). $[\alpha]_D^{20} = -18.8°$ (c=1.8 in $CH_2Cl_2$).

EXAMPLE 7

7EG-Tmsal-Bly-F₂Chaton-NHiBu 23 mg of the title compound of example 6 are dissolved in 1 ml of dry methylene chloride, and mixed with 130 mg of Collin's reagent. After 30 minutes, the product is filtered over silica gel, washed with ethyl acetate and concentrated by evaporation. $[\alpha]_D^{20} = -20.6°$ (c=0.3 in $CH_2Cl_2$).

EXAMPLE 8

3EG-Phe-His-Cha(OH)Bly-NHBu 223 mg of H-Phe-His-Cha(OH)Bly-NHBu in 2 ml of dimethylformamide are reacted analogously to example 1 with 60 g of hydroxybenzotriazole, 85 mg of 3EG-OH and 80 mg of N,N'-dicyclohexylcarbodiimide. The crude product is purified on silica gel with methanol/methylene chloride (5:95). $[\alpha]_D^{20} = -23.2°$ (c=0.15 in $CH_2Cl_2$).

EXAMPLE 9

7EG-Phe-Nle-Cha(OH)Bly-NHBu 200 mg of H-Phe-Nle-Cha(OH)Bly-NHBu are reacted analogously to example 1 in 2 ml of dimethylformamide with 50 mg of hydroxybenzotriazole, 140 mg of 7EG-OH and 70 mg of N,N'-dicyclohexylcarbodiimide. The crude product is crystallised from methylene chloride/ether/hexane. $[\alpha]_D^{20} = -31.3°$ (c=0.1 in $CH_2Cl_2$).

EXAMPLE 10

AcGlyc-4eg-Phe-Nle-Cha(OH)BlyNH-Bu 115 mg of AcGlyc-4eg-p-nitrophenol are refluxed for 24 hours with 100 mg of H-Phe-Nle-Cha(OH)GlyNH-Bu in 5 ml of tetrahydrofuran, whilst adding 20 mg of dimethylaminopyridine and 20 mg of N-methylmorpholine. The crude product is dissolved in ethyl acetate, extracted with aqueous Na-bicarbonate solution, dried over magnesium sulphate, concentrated by evaporation and recrystallised from methylene chloride/ether. The title compound has a $[\alpha]_D^{20} = -80°$ (c=0.05 in $CH_2Cl_2$).

EXAMPLE 11

Glyc-4eg-Phe-Nle-Cha(OH)BlyNH-Bu 100 mg of the tetraacetate of example 10 are dissolved in 1 ml of methanol, and mixed with a few drops of a 5% solution of sodium methylate in methanol. After 1 hour, the product is diluted with ethyl acetate, washed with aqueous Na bicarbonate solution, dried over magnesium sulphate, concentrated by evaporation and crystallised from methanol/methylene chloride/ether. The title compound has a $[\alpha]_D^{20} = -33.6°$ (c=0.1 in $MeOH/CH_2Cl_2$ [1:1]).

EXAMPLE 12

Stear-4eg-Phe-Nle-Cha(OH)BlyNH-Bu 340 mg of stear-4eg-p-nitrophenol are reacted analogously to example 10 with 290 mg of H-Phe-Nle-Cha(OH)BlyNH-Bu, 60 mg of N-methylmorpholine and 30 mg of dimethylaminopyridine. The crude product is chromatographed with 2% methanol in methylene chloride and crystallised from methylene chloride/ether. The title compound has a $[\alpha]_D^{20} = -18.0°$ (c=0.15 in $CH_2Cl_2$).

EXAMPLE 13

H-4eg-Phe-Nle-Cha(OH)BlyNH-Bu 32 mg of the stearate of example 12 are cleaved with sodium methylate in methanol analogously to example 11. The title compound has a $[\alpha]_D^{20} = -24.3°$ (c=0.1 in $CH_2Cl_2$).

EXAMPLE 14

Linol-4eg-Phe-Nle-Cha(OH)BlyNH-Bu 450 mg of linol-4eg-p-nitrophenol are reacted analogously to example 10 with 400 mg of H-Phe-Nle-Cha(OH)BlyNH-Bu, 90 mg of N-methylmorpholine and 30 mg of dimethylamino-pyridine. After chromatography on silica gel with 3% methanol in methylene chloride, there follows recrystallisation from methylene chloride/ether. The title compound has a $[\alpha]_D^{20} = -17.1°$ (c = 0.15 in $CH_2Cl_2$).

EXAMPLE 15

Dinac-4eg-Phe-Nle-Cha(OH)BlyNH-Bu 525 mg of dinac-4eg-p-nitrophenol are reacted analogously to example 10 with 400 mg of H-Phe-Nle-Cha(OH)BlyNH-Bu, 80 mg of N-methylmorpholine and 30 mg of dimethylaminopyridine. The product is chromatographed with 6% methanol in methylene chloride and is crystallised from methylene chloride/ether. The title compound has a $[\alpha]_D^{20} = -16.8°$ (c = 0.15 in $CH_2Cl_2$).

EXAMPLE 16

Chol-4eg-Phe-Nle-Cha(OH)BlyNH-Bu 600 mg of chol-4eg-p-nitrophenol are reacted exactly as in example 10 with 300 mg of H-Phe-Nle-Cha(OH)-BlyNH-Bu, 70 mg of N-methylmorpholine and 30 mg of dimethylaminopyridine. The crude product is recrystallised from methanol/methylene chloride/ether.

EXAMPLE 17

BOC-Gly-4eg-Phe-Nle-Cha(OH)BlyNH-Bu 540 mg of BOC-Gly-4eg-p-nitrophenol are reacted analogously to example 10 with 500 mg of H-Phe-Nle-Cha(OH)BlyNH-Bu, 110 mg of N-methylmorpholine and 30 mg of dimethylaminopyridine. The crude product is recrystallised from methylene chloride/ether. The title compound has a $[\alpha]_D^{20} = -23.6°$ (c = 0.1 in $CH_2Cl_2$).

EXAMPLE 18

H-Gly-4eg-Phe-Nle-Cha(OH)BlyNH-Bu.HCl 400 mg of the title compound of example 17 are dissolved in 4 ml of methylene chloride and mixed at 0°–5° with 4 ml of trifluoroacetic acid. After ½ hour, the solution is partitioned between aqueous 2N soda solution and methylene chloride, the organic phase is dried over potassium carbonate and concentrated by evaporation. The residue is dissolved in methanol, mixed with 0.1 ml of conc. hydrochloric acid, concentrated by evaporation and crystallised from methanol/methylene chloride/ether. The title compound has a $[\alpha]_D^{20} = -30.0°$ (c = 0.1 in MeOH/$CH_2/Cl_2$ [1:1]).

EXAMPLE 19

3EG-Cha-His-Cha(OH)BlyNH-Bu 500 mg of H-Cha-His-Cha(OH)BlyNH-Bu are reacted analogously to example 1 with 200 mg of 3EG-OH, 120 mg of 1-hydroxybenzotriazole and 0.13 ml of dicyclohexylcarbodiimide in dimethylformamide. The crude product is chromatographed with 10% methanol/methylene chloride, and is crystallised from methanol/methylene chloride/ether. The title compound has a $[\alpha]_D^{20} = -34.0°$ (c = 0.1 in MeOH/$CH_2Cl_2$ [1:1]).

EXAMPLE 20

(2S,3S)-3-(3EG-Phe-Nle)-amido-1-(isopropylcarbamoyl)amino-4-cyclohexyl-2-butanol The title compound is obtained analogously to example 4 from 284 mg of (2S,3S)-3-(H-Phe-Nle)amido-1-(isopropylcarbamoyl)-amino-4-cyclohexyl-2-butanol.-hydrochloride, (obtainable by means of BOC cleavage according to known processes from (2S,3S)-3-(N-BOC-Phe-Nle-)amido-1-(isopropylcarbamoyl)amino-4-cyclohexyl-2-butanol), 111 mg of 3EG-OH, 156 mg of 1-hydroxybenzotriazole, 99 mg of N-ethyl-N'-(3-dimethylaminopropyl)-carbodiimide.hydrochloride and 0.07 ml of triethylamine. It has a m.p. of 125°–128°, $[\alpha]_D^{20} = -12.4°$ (c = 1 in methanol).

The starting compound used in example 20, (2S,3S)-3-(N-BOC-Phe-Nle)amido-1-(isopropylcarbamoyl)amino-4-cyclohexyl-2-butanol, is obtained as follows:

A solution of 273 mg of (2S,3S)-1-amino-3-(N-BOC-phenylalaninylnorleucyl)-amido-4-cyclohexyl-2-butanol in 10 ml of anhydrous tetrahydrofuran is mixed at 0° with 0.055 ml of isopropylisocyanate, stirred for 1 hour at room temperature and concentrated by evaporation under a high vacuum. Crystallisation of the residue from methylene chloride/methanol/hexane yields the title compound. M.p. 167°–168° C. (decomp.), $[\alpha]_D^{20} = -16.2°$ (c = 1 in methanol).

The starting product used in this example may be produced as follows:

a) (2S,3S)-3-BOC-amino-1-Cbz.-amino-4-cyclohexyl-2-butanol 4.18 ml of benzyl chloroformate are added at a temperature of 2° to 5° to a solution of 5.28 ml of triethylamine and 6.3 g of (2S,3S)-1-amino-3-BOC-amino-4-cyclohexyl-2-butanol in 120 ml of dichloromethane, and the solution obtained is stirred for 30 minutes at room temperature. The solution is then diluted with dichloromethane and washed with 0.25N hydrochloric acid, saturated aqueous sodium bicarbonate solution and water. The organic phase is dried over sodium sulphate and evaporated under vacuum. Chromatography of the residue on silica gel using toluene/ethyl acetate (3:1) as the eluant yields (2S,3S)-3-BOC-amino-1-Cbz-amino-4-cyclohexyl-2-butanol as a slightly yellowish oil.

b) (2S,3S)-3-amino-1-Cbz-amino-4-cyclohexyl-2-butanol 8.06 g of the (2S,3S)-compound obtained in section a) are added whilst cooling to 80 ml of the mixture of acetic acid/conc. hydrochloric acid (9:1), and the solution obtained is stirred at room temperature for 1 hour and then evaporated to dryness. The hydrochloride of the above title compound is thus obtained as a colourless foam.

c) (2S,3S)-3-(BOC-phenylalaninyl-norleucinyl)amino-1-Cbz-amino-4-cyclohexyl-2-butanol 4.06 ml of diphenylphosphoryl-azide and 4.94 ml of triethylamine are gradually added to an ice-cooled solution of 6.68 g of BOC-Phe-Nle-OH and 6.3 g of crude hydrochloride of the (2S,3S)-compound described in section b) in dimethylformamide, and the clear solution obtained is stirred over night at room temperature, then concentrated under vacuum, taken up in dichloromethane, and the dichloromethane solution is washed with 0.25N hydrochloric acid, saturated aqueous sodium bicarbonate solution and water, and dried over anhydrous sodium sulphate. After evaporation under vacuum, the residue is chromatographed on silica gel [dichloromethane/ethanol (49:1) as the eluant] and the product obtained is crystallised from dichloromethane/hexane. The title compound thus obtained melts at 167°–168° (decomp.).

d) (2S,3S)-1-amino-3-(BOC-phenylalaninyl-norleucinyl)-amino-4-cyclohexyl-2-butanol 7.0 g of the (2S,3S)-compound obtained in section c) and 0.7 g of palladium on active charcoal (10%) in 140 ml of methanol are hydrogenated for 1½ hours at room temperature in a hydrogen atmosphere at atmospheric pressure, and the mixture is subsequently diluted with dichloromethane and filtered through Celite. After evaporation of the filtrate under vacuum and crystallisation of the residue from methanol/ether, the title compound is obtained as colourless crystals having a m.p. of 140°–141°, $[\alpha]_D^{20} = -38.5°$ (c=1 in methanol).

EXAMPLE 21

3EG-Tmsal-His-Cha(OH)Bly-NHBu 500 mg of H-Tmsal-His-Cha(OH)Bly-NHBu are reacted analogously to example 1 in dimethylformamide with 206 mg of 3EG-OH, 110 mg of hydroxybenzotriazole and 144 mg of diisopropylcarbodiimide. The crude product is chromatographed with methanol/methylene chloride (2–10%). $[\alpha]_D^{20} = -27.6°$ (c=0.1 in $CH_2Cl_2$).

EXAMPLE 22

Clof-4eg-Phe-Nle-Cha(OH)Bly-NHBu 700 mg of H-Phe-Nle-Cha(OH)Bly-NHBu and 700 mg of Clof-4eg-p-nitrophenol are dissolved in a small amount of dimethylformamide and after addition of 50 mg of 4-dimethylaminopyridine the mixture is heated to 40° during 15 hours. After partitioning between ethylacetate and a saturated aquous sodium bicarbonate solution the organic phase is separated, dried and evaporated. The crude product is recrystallised from methylene chloride/methanol/ether. $[\alpha]_D^{20} = -16.7°$ (c=0.8 in $CH_2Cl_2$).

EXAMPLE 23

7EG-Tmsal-His-Cha(OH)Bly-NHBu 500 mg of H-Tmsal-His-Cha(OH)Bly-NHBu are reacted analogously to example 1 in a small amount of dimethylformamide with 338 mg of 7EG-OH, 110 mg of hydroxybenzotriazole and 131 ml of diisopropylcarbodiimide. The crude product is chromatographed with methanol/methylene chloride (5:95). The title compound has a $[\alpha]_D^{20} = 21.0°$ (c=0.1 in $CH_2Cl_2$).

EXAMPLE 24

Me3eg-Tmsal-His-Chatin-Leu-α-Pic 700 mg of H-Tmsal-His-Chatin-Leu-α-Pic are reacted analogously to example 22 with 350 mg of Me3eg-p-nitrophenol and 500 mg of 4-dimethylaminopyridine. The crude product is chromatographed with methanol/methylene chloride (1–10%). The title compound has a $[\alpha]_D^{20} = -26.5°$ (c=0.2 in $CH_2Cl_2$).

EXAMPLE 25

Me3eg-Tmsal-(Me3eg)His-Chatin-Leu-α-Pic

According to example 24 the title compound acylated on the histidine moiety is obtained as by product. $[\alpha]_D^{20} = -4.7°$ (c=0.8 in $CH_2Cl_2$).

EXAMPLE 26

3EG-Phe-Nle-Cha(OH)CH$_2$PO(OMe)$_2$ 830 mg of H-Phe-Nle-CHa(OH)CH$_2$PO(OMe)$_2$ in 15 ml of dimethylformamide/tetrahydrofurane (1:1) are reacted with 310 mg of hydroxybenzotriazole, 330 mg of 3EG-OH and 300 mg of N-ethyl-N'-(3-dimethylaminopropyl)-carbodiimide-hydrochloride (EDCI). After 24 hours the mixture is evaporated and to the residue an aqueous sodium bicarbonate solution is added at 0°. The precipitate is dissolved in ethylacetate and the organic phase first washed with 2N hydrochloric acid and then with a saturated aqueous sodiumchloride solution. After drying over sodiumsulphate and evaporation the crude product is purified on silicagel with methylene chloride/ethanol (19:1). The title compound has a $[\alpha]_D^{25} = -38.7°$ (c=0.5 in $CH_2Cl_2$).

EXAMPLE 27

Niacin-2eg-Tmsal-Nle-F$_2$-Chatin-NHiBu 553 mg of H-Tmsal-Nle-F$_2$-Chatin-NHiBu are reacted analogously to example 22 with 381 mg of Niacin-2eg-p-nitrophenol. The title compound has a $[\alpha]_D^{20} = -24.5°$ (c=0.1 in $CH_2Cl_2$).

EXAMPLE 28

Niacin-2eg-Tmsal-Nle-F$_2$-Chaton-NHiBu 600 mg of the title compound of example 27 are oxidised analogously to example 7 with 3.1 g of Collin's reagens. $[\alpha]_D^{20} = -32.6°$ (c=0.8 in $CH_2Cl_2$).

EXAMPLE 29

Me(OCH$_2$CH$_2$)$_2$-Phe-Nle-Cha(OH)Bly-NHBu 100 mg of H-Phe-Nle-Cha(OH)Bly-NHBu are reacted in dimethylformamide with 50 mg of 3,6,9-trioxadecyljodide and 50 mg of ethyldiisopropylamine. After 100 hours the reaction product is isolated and chromatographed with methanol/methylene chloride (1–10%). $[\alpha]_D^{20} = -46.5°$ (c=0.15 in $CH_2Cl_2$).

EXAMPLE 30

7EG-Tmsal-Nle-Chatin-Leu-α-Pic 400 mg of H-Tmsal-Nle-Chatin-Leu-α-Pic are reacted analogously to example 1 with 260 mg of 7EG-OH, 80 mg of hydroxybenzotriazole and 130 mg of N,N'-dicyclohexylcarbodiimide. The crude product is chromatographed with 5% methanol in methylene chloride. $[\alpha]_D^{20} = -3.9°$ (c=0.8 in $CH_2Cl_2$).

EXAMPLE 31

Niacin-2eg-Tmsal-Nle-Chatin-Leu-α-Pic 500 mg of H-Tmsal-Nle-Chatin-leu-α-Pic are reacted analogously to example 22 in dimethylformamide with 300 mg of Niacin-2eg-p-nitrophenol. The crude product is cristallised from methylene chloride/ether. $[\alpha]_D^{20} = -27.2°$ [c=0.25 in $CH_2Cl_2$/MeOH (1:1)].

EXAMPLE 32

H-2eg-Tmsal-Nle-F$_2$-Chaton-NHiBu 32 mg of the title compound of example 28 are dissolved in methanol and hydrolised with 4 mg sodiumhydroxide. The reaction mixture is partitioned between aqueous sodium bicarbonate and methylene chloride, the organic phase dried and evaporated $[\alpha]_D^{20} = -27.1°$ (c=0.6 in $CH_2Cl_2$).

EXAMPLE 33

3EG-Phe-Cha(OH)Bualy-NHBu 325 mg of H-Phe-Nle-Cha(OH)Bualy-NHBu in 6 ml of dimethylformamide/tetrahydrofurane (1:1) are reacted analogously to example 26 with 193 mg of hydroxybenzotriazole, 118 mg of 3EG-OH and 210 mg of N-ethyl-N'-(3-dimethylaminopropyl)-carbodiimide.HCl. The crude product is purified on silicagel with methylene chloride/ethanol (19:1). $[\alpha]_D^{25} = -18.7°$ (c=0.475 in $CH_2Cl_2$).

EXAMPLE 34

Tmpac-2eg-Tmsal-Nle-$F_2$-Chatin-NHiBu 440 mg of H-Tmsal-Nle-$F_2$-Chatin-NHiBu are reacted analogously to example 22 with 370 mg of H-Tmpac-2eg-p-nitrophenol. The crude product is purified by chromatography on silicagel. $[\alpha]_D^{20} = -19.3°$ (c=0.1 in $CH_2Cl_2$).

EXAMPLE 35

Tmpac-2eg-Tmsal-Nle-$F_2$-Chaton-NHiBu 20 mg of title compound of example 34 are oxidised analogously to example 7 with 100 mg of Collin's reagens. $[\alpha]_D^{20} = -21.0°$ (c=0.2 in $CH_2Cl_2$).

EXAMPLE 36

3EG-Ada-Nle-Cha(OH)$CH_2$CHCl-NHBu 352 mg of H-Ada-Nle-Cha(OH)$CH_2$CHCl-NHBu.HCl in 3.5 ml of dimethylformamide/tetrahydrofurane (1:1) are reacted analogously to example 26 with 120 mg hydroxybenzotriazole, 0.0815 ml of N-ethylmorpholine, 174 mg of 3EG-OH and 105 mg of N-ethyl-N'-(3-dimethylaminopropyl)-carbodiimide.HCl. The crude product is purified on silicagel (Lichroprep 25-40) with methylene chloride/ethanol (49:1). $[\alpha]_D^{20} = -14.9°$ (c=0.53 in $CH_2Cl_2$).

EXAMPLE 37

3EG-Tmsal-Nle-Cha(OH)Bly-NHBu 502 mg of H-Tmsal-Nle-Cha(OH)Bly-NHBu in 2.3 ml of tetrahydrofurane/dimethylformamide (1:1) are reacted analogously to example 26 with 208 mg of hydroxybenzotriazole, 151 mg of 3EG-OH and 143 mg of N-ethyl-N'-(3-dimethylaminopropyl)-carbodiimide.HCl. The crude product is cristalised from methylene chloride/hexane. $[\alpha]_D^{20} = -31.4°$ (c=0.50 in $CH_2Cl_2$).

EXAMPLE 38

3EG-Tmsal-Nle-Cha(OH)$CH_2$CHCl-NHBu 338 mg of H-Tmsal-Nle-Cha(OH)$CH_2$CHCl-NHBu.HCl in 3.7 ml of dimethylformamide/tetrahydrofurane (1:1) are reacted analogously to example 26 with 127 mg of hydroxybenzotriazole, 0.0862 ml of N-ethylmorpholine, 184 mg of 3EG-OH and 111 mg of N-ethyl-N'-(3-dimethylaminopropyl)-carbodiimide.HCl. The crude product is chromatographed on silica gel (Lichroprep RP-18, 40-63) with methanol/water (8:2). $[\alpha]_D^{25} = -22.8°$ (c=0.6 in $CH_2Cl_2$).

EXAMPLE 39

3EG-Ada-Nle-Cha(OH)$CH_2$CHF-NHBu 490 mg of H-Ada-Nle-Cha(OH)$CH_2$CHF-NHBu.HCl in 5.0 ml dimethylformamide/tetrahydrofurane (1:1) are reacted analogously to example 26 with 172 mg of hydroxybenzotriazole, 0.0986 ml of N-methylmorpholine, 248 mg of 3EG-OH and 150 mg of N-ethyl-N'-(3-dimethylaminopropyl)-carbodiimide.HCl. The crude product is purified on silicagel (Lichroprep RP-18, 40-63) with acetonitrile/water (8:2). $[\alpha]_D^{25} = -21.8°$ (c=0.33 in $CH_2Cl_2$).

EXAMPLE 40

3EG-Phe-Nle-Cha(OH)$CH_2$CHCl-NHBu 614 mg of H-Phe-Nle-Cha(OH)$CH_2$CHCl-NHBu.HCl in 6.5 ml dimethylformamide/tetrahydrofurane (1:1) are reacted analogously to example 26 with 224 mg of hydroxybenzotriazole, 0.127 ml of N-Methylmorpholine, 324 mg of 3EG-OH and 196 mg of N-ethyl-N'-(3-dimethylaminopropyl)-carbodiimide.HCl. The crude product is cristallised from ethanol/ether/hexane. $[\alpha]_D^{25} = -19.8°$ (c=0.555 in MeOH).

EXAMPLE 41

3EG-Ada-Nle-Cha(OH)Fala-NHBu 280 mg of H-Ada-Nle-Cha(OH)Fala-NHBu in 2.8 ml of dimethylformamide/tetrahydrofurane (1:1) are reacted analogously to example 26 with 96 mg of hydroxybenzotriazole, 0.055 ml of N-methylmorpholine, 139 mg of 3EG-OH and 84 mg of N-ethyl-N'-(3-dimethylaminopropyl)-carbodiimide.HCl. The crude product is purified on silicagel with methylene chloride/ethanol (49:1). $[\alpha]_D^{25} = -35.4°$ (c=0.48 in $CH_2Cl_2$).

EXAMPLE 42

3EG-Cha(OH)Bly-NHBu 340 mg of H-Cha(OH)Bly-NHBu, 220 mg of 3EG-OH, 310 mg of N,N'-dicyclohexylcarbodiimide and 310 mg of 1-hydroxybenzotriazole are reacted in 10 ml of dimethylformamide analogously to example 1. $[\alpha]_D^{20} = -22.7°$ (c=1 in methylene chloride).

EXAMPLE 43

3EG-Ada-Nle-Cha(OH)$CH_2$CH($N_3$)-NHBu 387 mg of H-Ada-Nle-Cha(OH)$CH_2$CH($N_3$)-NHBu in 3.9 ml of dimethylformamide/tetrahydrofurane (1:1) are reacted analogously to example 26 with 135 mg of hydroxybenzotriazole, 196 mg of 3EG-OH and 118 mg of N-ethyl-N'-(3-dimethylaminopropyl)-carbodiimide.HCl. The crude product is chromatographed on neutral aluminiumoxide (akt. III) with methylene chloride/ethanol (19:1). The title product is lyophilisated with benzene. $[\alpha]_D^{25} = -16.4°$ (c=0.555 in $CH_2Cl_2$).

EXAMPLE 44

3EG-Phe-Nle-Cha(OH)$CH_2$CH(S-iPr)-NHBu 416 mg of H-Phe-Nle-Cha(OH)$CH_2$CH(S-iPr)-NHBu in 4.5 ml of dimethylformamide/tetrahydrofurane (1:1) are reacted analogously to example 26 with 154 mg of hydroxybenzotriazole, 224 mg of 3EG-OH and 135 mg of N-ethyl-N'-(3-dimethylaminopropyl)-carbodiimide.HCl. The crude product is purified on neutral aluminiumoxide (akt. III) with methylene chloride/ethanol (49:1-19:1) and then crystallised from methylene chloride/ether/hexane. $[\alpha]_D^{25} = -17.1°$ (c=0.25 in MeOH).

EXAMPLE 45

3EG-His-Cha(OH)Bly-NHBu 440 mg of 3EG-OH, 1.15 g of H-His-Cha(OH)Bly-NHBu, 620 mg of 1-hydroxybenzotriazole and 420 mg of N,N'-dicyclohexylcarbodiimide are reacted in 20 ml of dimethylformamide analogously to example 1. M.p. 128°–130°, $[\alpha]_D^{25} = -33.0°$ (c=1 in methanol).

EXAMPLE 46

3EG-Thala-Nle-Chatin-Leu-α-Pic 260 mg of H-Thala-Nle-Chatin-Leu-α-Pic are reacted analogously to example 1 in 3 ml dimethylformamide with 100 mg of hydroxybenzotriazole, 84 mg of 3EG-OH and 78 mg of N,N'-dicyclohexylcarbodiimide. The crude product is chromatographed on silica gel with methylene chloride containing 7% ethanol. $[\alpha]_D^{20} = -16.7°$ (c=0.37 in ethanol).

The compounds according to the invention exhibit pharmacological activity and are, therefore, useful as pharmaceuticals.

They are inhibitors of renin activity, e.g. on human tetradecapeptide substrate at a concentration of $10^{-5}M$ to $10^{-11}M$ they inhibit the enzyme activity of pure human renin by 50% according to the method of F. Cumin et al. (Bioch. Biophys. Acta 913, 10 to 19 (1987)) or in a renin binding assay.

In the antibody-trapping method of K. Poulsen and J. Jorgensen (J. Clin. Endocrin. Metab. 39, [1974] 816-825), they inhibit human plasma renin activity at a concentration of $10^{-5}M$ to $10^{-11}M$.

The compounds according to the invention are therefore useful for the prophylaxis and treatment of conditions which are characterised by enzymatic malfunction and for which an inhibition of enzymatic activity is indicated.

As renin inhibitors they are suitable e.g. for use in the prophylaxis and treatment of hypertension and cardiac insufficiency ("congestive heart failure").

The compounds which are preferred for the prophylaxis and treatment of hypertension and cardiac insufficiency are the title compounds of examples 2, 3, 8 to 11, 13, 18, 19, 21 and 46, especially of examples 8 to 11, 13, 21 and 46, particularly of examples 13, 21 and 46, most preferred the compound of example 46.

The title compound of example 46 is the most preferred compound for the renin inhibition, it has for example been determined in the antibody trapping test having the lowest inhibiting concentration 0,15 nM/l, the highest inhibiting concentration 15 nM/l, $IC_{50}=1,5$ nM/l, it is therefore indicated that the compound of example 46 may be administered to larger mammals such as humans at daily dosage from 1 mg to 10 mg.

The compounds according to the invention exhibit also an antiretroviral activity and are therefore useful for the treatment of diseases caused by retroviruses including HTLV-I and -III. This activity can be demonstrated in the FeLV cat model [Cerny and Essex, CRC press in 1979, pp. 233–256; Cockerell et al., J. Natl. Cancer Inst. 57, 1095–1099 (1976); Cotter et al. J. Am. Vet. med. Assoc. 166, 449–453 (1975); Essex et al. Science 190, 790–792 (1975)]- a disease model for human AIDS.

It has been reported e.g. (25th ICAAC in Minneapolis, Sept. 30th–Oct. 2nd) that with a 30 mg treatment of 3'-azido-3'-deoxy-thymidine over 14 days a reduction of FeLV-titres by a factor of 10 could be shown, but no cure was achieved. On administration of the compounds of the invention, eradication of the virus can be observed. Dosage ranges for the anti-retro-viral activity are those conventionally employed and lie e.g. in the range of 5–20 mg/kg/day.

For above indications, the dosage to be administered depends on the compound respectively used, the type of administration and the desired treatment. In general, satisfactory results are obtained if the compounds are administered in a daily dosage of 0.02 mg/kg to ca. 20 mg/kg animal body weight. For larger mammals, for example humans an indicated daily dosage is from about 1 mg to about 500 mg, conveniently administered e.g. orally in doses of 0.25 mg to ca. 500 mg up to 4 times daily e.g. in divided form.

The compounds according to the invention may be administered in free form, or if acidic or basic groups are present, in pharmacologically acceptable salt form. Such salt forms have the same order of activity as the free forms and can be produced in known manner. The present invention similarly relates to pharmaceutical preparations containing a compound according to the invention in free form or in pharmaceutically acceptable salt form, optionally together with pharmaceutically adjuvants and/or carrier substances. Such pharmaceutical preparations may be formulated for use in enteral, preferably oral administration, e.g. at tablets, or for use in parenteral administration, e.g. as injectable solutions or suspensions. Further a nasal administration of the compounds according to the invention is also possible. An appropriate nasal spray can be prepared in a manner known per se.

What we claim is:

1. Hydrophilic renin inhibitors of formula $$R_1-O+(CH_2)_o-O)_m-(CH_2)_n-W-\overset{O}{\underset{\|}{C}}-A-B-C-D$$

wherein

W is —O—, —NR$_2$— or —CH$_2$, whereby R$_2$ signifies hydrogen or a straight-chain or branched (C$_{1-5}$)alkyl radical, R$_1$ is pyridinoyl;

R$_2$ is defined as above;

m is a whole number from 1 to 20, n is a whole number from 0 to 5, and o is 2 or 3, A, B and C are the same or different and signify a bond or a group of formula $$\begin{array}{c} R_3 \\ | \\ \diagdown N-C-C \\ | \quad \| \\ R_2 \quad O \end{array}$$

wherein

R$_2$ is defined as above, and

R$_3$ signifies a hydrophilic or lipophilic amino acid side chain, or

R$_2$ and R$_3$ together form a —(CH$_2$)$_o$— chain, wherein o is defined as above, D signifies either a group of formula

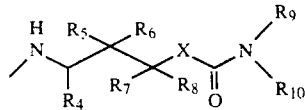

wherein
R₄ has the same significance as R₃,
R₅ is hydroxyl or an amino group, and
R₆ is hydrogen, or
R₅ and R₆ together form an oxo group,
R₇ and R₈, independently of one another, signify fluorine or hydrogen;
R₉ and R₁₀ are the same or different and respectively signify hydrogen, a straight-chain or branched (C₁₋₅)-alkyl radical, or they respectively signify a group of formula

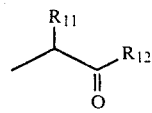

wherein
R₁₁ signifies a straight-chain or branched (C₁₋₅)-alkyl radical or a straight-chain or branched (C₁₋₅)-hydroxyalkyl radical;
R₁₂ is a hydroxyl radical, a straight-chain or branched (C₁₋₅)-alkoxy group, an amino group or a (C₁₋₅)-alkylamino group, an aminomethylpyridyl group, a benzyl group or a group of formula

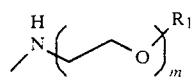

wherein
R₁ and m are defined as above, or R₁ denote a protected or unprotected amino acid;
X signifies a bond or denotes

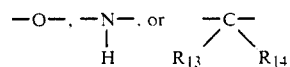

wherein
R₁₃ and R₁₄, independently of one another, denote hydrogen or fluorine, or respectively possess the definition given above for R₃, or
D signifies a group of formula

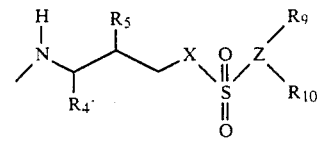

wherein
R₄, R₅, R₉, R₁₀ and X possess the definitions given above, and
Z is

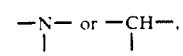

or
D signifies a group of formula

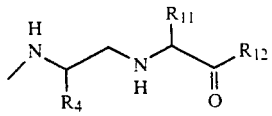

wherein
R₄, R₁₁ and R₁₂ possess the definitions given above, and their salts.

2. A compound of the formula:

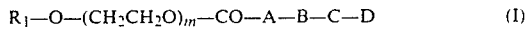

wherein
R₁ is pyridoyl,
m is an interger of from 2 to 7,
A, B, and C are each independently a bond or a group of the formula

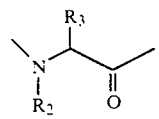

where
R₂ is hydrogen or straight or branched chain (C₁₋₅)alkyl and,
R₃ is cyclohexylmethyl, trimethylsilylmethyl, isobutyl, or 2-butenyl, and
D is a group of the formula

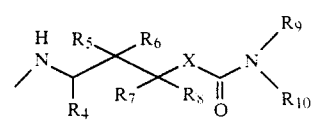

where
R₄ is the same as R₂,
R₅ is hydroxyl and R₆ is hydrogen or
R₅ and R₆ together are oxo,
R₇ and R₈ are each independently hydrogen or fluorine,
X is a bond,
R₉ is hydrogen and
R₁₀ is straight or branched chain (C₁₋₅)alkyl or a group of the formula

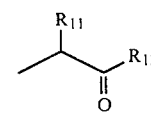

where
R₁₁ is straight or branched chain (C₁₋₅)alkyl and
R₁₂ is aminomethylpyridyl.

3. The compound according to claim 2, which is (3R,4S,7S,10R)-5,8,11-triaza-7-butyl-4-cyclohexylmethyl-2,2-difluoro-3-hydroxy-19-nicotinoyl-10-trimethylsilymethyl-13,16,19-trioxa-6,9,12-trioxo-nonadecanic acid isobutylamide.

4. The compound according to claim 2, which is (4S,7S,10R)-5,8,11-triaza-7-butyl-4-cyclohexylmethyl-2,2-difluoro-19-nicotinoyl-10-trimethylsilymethyl- 13,16,19-trioxa-3,6,9,12-tetraoxo-nonadecanic acid isobutylamide.

5. The compound according to claim 2, which is (3S,4S,7S,10R)-5,8,11-triaza-7-butyl-4-cyclohexylmethyl-3-hydroxy-19-nicotinoyl-10-trimethylsilylmethyl-13,16,19-trioxa-6,9,12-trioxo-nonadecanoyl-(L)-leuzine-(2-picolylamide).

6. A method of preventing or treating diseases caused by retroviruses which comprises administering to an animal in need of such treatment a therapeutically effective amount of a compound of claim 1.

7. A pharmaceutical composition useful in treating diseases caused by retroviruses comprising an appropriate amount of a compound of claim 1 in free form or in pharmaceutically acceptable salt form, in association with a pharmaceutical carrier or diluent.

* * * * *